(12) United States Patent
Soetikno et al.

(10) Patent No.: US 10,750,943 B2
(45) Date of Patent: Aug. 25, 2020

(54) IMAGING-GUIDED CREATING AND MONITORING OF RETINAL VASCULAR OCCLUSIVE DISEASE

(71) Applicant: Northwestern University, Evanston, IL (US)

(72) Inventors: Brian T. Soetikno, Chicago, IL (US); Xiao Shu, Evanston, IL (US); Hao F. Zhang, Deerfield, IL (US)

(73) Assignee: NORTHWESTERN UNIVERSITY, Evanstone, IL (US)

( * ) Notice: Subject to any disclaimer, the term of this patent is extended or adjusted under 35 U.S.C. 154(b) by 0 days.

(21) Appl. No.: 16/005,093

(22) Filed: Jun. 11, 2018

(65) Prior Publication Data
US 2018/0353064 A1    Dec. 13, 2018

Related U.S. Application Data

(60) Provisional application No. 62/517,341, filed on Jun. 9, 2017.

(51) Int. Cl.
*A61B 3/10* (2006.01)
*A61B 3/12* (2006.01)
(Continued)

(52) U.S. Cl.
CPC ............ *A61B 3/102* (2013.01); *A61B 3/1025* (2013.01); *A61B 3/12* (2013.01); *A61K 49/0041* (2013.01);
(Continued)

(58) Field of Classification Search
CPC ........... A61B 3/14; A61B 3/0025; A61B 3/12; A61B 3/102; A61B 3/0008
(Continued)

(56) References Cited

U.S. PATENT DOCUMENTS

| 5,053,006 | A | 10/1991 | Watson |
| 8,574,277 | B2 * | 11/2013 | Muller ................. A61F 9/0008 607/88 |

(Continued)

FOREIGN PATENT DOCUMENTS

| WO | WO 2001-058240 | 8/2001 |
| WO | WO 2016-151491 | 9/2016 |

OTHER PUBLICATIONS

Vakhtin et al.. "Common-path interferometer for frequency-domain optical coherence tomography," Applied Optics. 42(34): 6953-6958 (Dec. 2003).
(Continued)

*Primary Examiner* — Mohammed A Hasan
(74) *Attorney, Agent, or Firm* — Leydig, Voit & Mayer, Ltd.

(57) ABSTRACT

The present disclosure provides systems and methods for imaging-guided monitoring and modeling of retinal vascular occlusive conditions. An example integrated optical coherence tomography (OCT) and scanning laser ophthalmoscope (SLO) apparatus includes an OCT subsystem to acquire baseline OCT and OCT angiography (OCTA) volumes of a subject without dye before occlusion and subsequent OCT and OCTA volumes of the subject with dye after occlusion. The example apparatus includes an SLO subsystem including a laser controlled to adjust a laser to form a vascular occlusion at a location on a target vessel of the subject. The example apparatus includes a processor to process the OCT and OCTA volumes and feedback from the OCT subsystem and the SLO subsystem to determine a change in three-dimensional vasculature from before the vascular occlusion to after the vascular occlusion.

23 Claims, 11 Drawing Sheets

(51) Int. Cl.

| | |
|---|---|
| A61K 49/00 | (2006.01) |
| A61F 9/008 | (2006.01) |
| A61K 41/00 | (2020.01) |
| G03F 7/027 | (2006.01) |

(52) U.S. Cl.
CPC ...... *A61K 49/0071* (2013.01); *A61F 9/00817* (2013.01); *A61F 9/00821* (2013.01); *A61F 2009/00851* (2013.01); *A61F 2009/00863* (2013.01); *A61F 2009/00897* (2013.01); *A61K 41/0057* (2013.01); *G03F 7/027* (2013.01)

(58) Field of Classification Search
USPC ........................................................ 351/206
See application file for complete search history.

(56) References Cited

U.S. PATENT DOCUMENTS

| | | | |
|---|---|---|---|
| 9,360,660 | B2 | 6/2016 | Yi |
| 9,442,095 | B2 | 9/2016 | Jiao |
| 9,513,260 | B2 | 12/2016 | Zhang |
| 9,619,903 | B2 | 4/2017 | Yi |
| 9,962,075 | B2 | 5/2018 | Yi |
| 10,107,613 | B2 | 10/2018 | Jiao |
| 2012/0323228 | A1 | 12/2012 | Peyman |
| 2014/0185009 | A1* | 7/2014 | Imamura ............... A61B 3/152 351/208 |
| 2014/0276025 | A1* | 9/2014 | Durbin ................ A61B 5/4842 600/427 |
| 2017/0307440 | A1 | 10/2017 | Urban |
| 2018/0001581 | A1 | 1/2018 | Patel |
| 2018/0020922 | A1 | 1/2018 | Liu |
| 2018/0088048 | A1 | 3/2018 | Dong |
| 2018/0242844 | A1 | 8/2018 | Liu |
| 2018/0256025 | A1 | 9/2018 | Yi |
| 2018/0353064 | A1 | 12/2018 | Soetikno |
| 2019/0025476 | A1 | 1/2019 | Sun |
| 2019/0082952 | A1 | 3/2019 | Zhang |

OTHER PUBLICATIONS

U.S. Appl. No. 13/524,813 / US 2012-0320368 A1 / U.S. Pat. No. 9,442,095, filed Jun. 15, 2012 / Dec. 20, 2012 / Sep. 13, 2016, Issued.
U.S. Appl. No. 13/902,288 / US-2013-0314717-A1 / U.S. Pat. No. 9,360,660, filed May 24, 2013 / Nov. 28, 2013 / Jun. 7, 2016, Issued.
U.S. Appl. No. 14/299,807 / US-2014-0360273-A1 / U.S. Pat. No. 9,513,260, filed Jun. 9, 2014 / Dec. 11, 2014 / Dec. 6, 2016, Issued.
U.S. Appl. No. 14/698,641 / US-2015-0348287-A1 / U.S. Pat. No. 9,619,903, filed Apr. 28, 2015 / Dec. 3, 2015 / Apr. 11, 2017, Issued.
U.S. Appl. No. 15/514,084 / US-2017-0307440-A1, filed Mar. 24, 2017 / Oct. 26, 2017, Pending.
U.S. Appl. No. 15/251,610 / US-2016-0370167 A1 / U.S. Pat. No. 10,107,613, filed Aug. 30, 2016 / Dec. 22, 2016 / Oct. 23, 2018, Issued.
U.S. Appl. No. 15/465,285 / US-2017-0188818-A1 / U.S. Pat. No. 9,962,075, filed Mar. 21, 2017 / Jul. 6, 2017 / May 8, 2018, Issued.
U.S. Appl. No. 15/543,490 / US-2018-0001581-A1, filed Jul. 13, 2017 / Jan. 4, 2018, Pending.
U.S. Appl. No. 15/583,615 / US-2018-0020922-A1, filed May 1, 2017 / Jan. 25, 2018, Pending.
U.S. Appl. No. 15/584,018 / US-2018-0088048-A1, filed May 1, 2017 / Mar. 29, 2018, Pending.
U.S. Appl. No. 15/751,107 / US-2018-0242844-A1, filed Aug. 5, 2016 / Aug. 30, 2018, Pending.
U.S. Appl. No. 15/972,753 / US-2018-0256025-A1, filed May 7, 2018 / Sep. 13, 2018, Pending.
U.S. Appl. No. 16/005,093 / US-2018-0353064-A1, filed Jun. 11, 2018 / Dec. 13, 2018, Pending.
U.S. Appl. No. 16/068,819 / US-2019-0025476 -A1, filed Jul. 9, 2018 / Jan. 24, 2019, Pending.
U.S. Appl. No. 16/123,518 / US-2019-0082952 A1, filed Sep. 6, 2018 / Mar. 21, 2019, Pending.
Choi et al. (2015) "Ultrahigh-Speed, Swept-Source Optical Coherence Tomography Angiography in Nonexudative Age-Related Macular Degeneration with Geographic Atrophy," Ophthalmology 122(12): 2532-2544.
Derosa et al. (2002) "Photosensitized singlet oxygen and its applications," Coordin. Chem. Rev. 233-234: 351-371.
Dominguez et al. (2015) "Experimental Branch Retinal Vein Occlusion Induces Upstream Pericyte Loss and Vascular Destabilization," PLoS One 10(7), e0132644: pp. 1-14.
Ebneter et al. (2015) "Investigation of retinal morphology alterations using spectral domain optical coherence tomography in a mouse model of retinal branch and central retinal vein occlusion," PLoS One 10(3), e0119046: pp. 1-15.
Genevois et al. (2004) "Microvascular remodeling after occlusion-recanalization of a branch retinal vein in rats," Invest. Ophthalmol. Vis. Sci. 45(2): 594-600.
Giannakaki-Zimmermann et al. (Aug. 2016) "Optical Coherence Tomography Angiography in Mice: Comparison with Confocal Scanning Laser Microscopy and Fluorescein Angiography," Transl. Vis. Sci. Technol. 5(4), 11: pp. 1-9.
Gong et al. (2015) "Optimization of an Image-Guided Laser-Induced Choroidal Neovascularization Model in Mice," PLoS One 10(7), e0132643: pp. 1-15.
Hamilton et al. (1979) "Experimental retinal branch vein occlusion in rhesus monkeys. I. Clinical appearances," Br. J. Ophthalmol. 63: 377-387.
Hayreh (2005) "Prevalent misconceptions about acute retinal vascular occlusive disorders," Prog. Retin. Eye Res. 24: 493-519.
Hayreh (2014) "Ocular vascular occlusive disorders: natural history of visual outcome," Prog. Retin. Eye Res. 41: 1-25.
Jia et al. (2012) "Split-spectrum amplitude-decorrelation angiography with optical coherence tomography," Opt. Express 20(4): 4710-4725.
Kellogg et al. (1964) "Radiationless Intermolecular Energy Transfer. III. Determination of Phosphorescence Efficiencies," J. Chem. Phys. 41(10): 3042-3045.
Kleinfeld et al. (2019) "Targeted occlusion to surface and deep vessels in neocortex via linear and nonlinear optical absorption," Animal models of acute neurological injury: 145-162.
Kocaoglu et al. (2007) "Simultaneous fundus imaging and optical coherence tomography of the mouse retina," Invest. Ophthalmol. Vis. Sci. 48(3): 1283-1289.
Komar et al. (2013) "Multimodal instrument for high-sensitivity autofluorescence and spectral optical coherence tomography of the human eye fundus," Biomed. Opt. Express 4(11): 2683-2695.
Lee et al. (2011) "Motion correction for phase-resolved dynamic optical coherence tomography imaging of rodent cerebral cortex," Opt. Express 19(22): 21258-21270.
Linden et al. (1988) "Type I and type II sensitizers based on Rose Bengal onium salts," Photochem. Photobiol. 47(4): 543-550.
Liu et al. (2015) "Simultaneous optical coherence tomography angiography and fluorescein angiography in rodents with normal retina and laser-induced choroidal neovascularization," Opt. Lett. 40(24): 5782-5785.
Nanda et al. (1987) "A new method for vascular occlusion. Photochemical initiation of thrombosis," Arch. Ophthalmol. 105: 1121-1124.
Paques et al. (2003) "Structural and hemodynamic analysis of the mouse retinal microcirculation," Invest. Ophthalmol. Vis. Sci. 44(11): 4960-4967.
Rehak et al. (2009) "Retinal gene expression and Müller cell responses after branch retinal vein occlusion in the rat," Invest. Ophthalmol. Vis. Sci. 50(5): 2359-2367.
Rogers et al. (2010) "The prevalence of retinal vein occlusion: pooled data from population studies from the United States, Europe, Asia, and Australia," Ophthalmology 117(2):313-319.
Rosen et al. (2009) "Simultaneous OCT/SLO/ICG imaging," Invest. Ophthalmol. Vis. Sci. 50(2): 851-860.

(56) References Cited

OTHER PUBLICATIONS

Royster et al. (1988) "Photochemical initiation of thrombosis. Fluorescein angiographic, histologic, and ultrastructural alterations in the choroid, retinal pigment epithelium, and retina," Arch. Ophthalmol. 106: 1608-1614.

Shah et al. (Jul. 2016) "Visible-Light Optical Coherence Tomography Angiography for Monitoring Laser-Induced Choroidal Neovascularization in Mice," Invest. Ophthalmol. Vis. Sci. 57(9): OCT86-OCT95.

Shin et al. (2013) "Optically induced occlusion of single blood vessels in rodent neocortex," Cold Spring Harb. Protoc. 2013: 1153-1160.

Soetikno et al. (May 2018) "Longitudinal characterization of branch retinal vein occlusions created by image-guided photocoagulation," Northwestern University, Poster Presentation, 1 pp.

Soetikno et al. (May 2017) "Monitoring retinal vascular occlusions in rodents with OCT angiography," Northwestern University, Poster Presentation, 1 pp.

Soetikno et al. (Aug. 2017) "Optical coherence tomography angiography of retinal vascular occlusions produced by imaging-guided laser photocoagulation," Biomedical Optics Express 8(8): 3571-3582.

Song et al. (2012) "Integrating photoacoustic ophthalmoscopy with scanning laser ophthalmoscopy, optical coherence tomography, and fluorescein angiography for a multimodal retinal imaging platform," J. Biomed. Opt. 17(6): 061206-1-061206-7.

Sun et al. (2013) "Neuroprotective effect of minocycline in a rat model of branch retinal vein occlusion," Exp. Eye Res. 113: 105-116.

Zawadzki et al. (2011) "Integrated adaptive optics optical coherence tomography and adaptive optics scanning laser ophthalmoscope system for simultaneous cellular resolution in vivo retinal imaging," Biomed. Opt. Express 2(6): 1674-1686.

Zhang et al. (2005) "Activation of the mitochondrial apoptotic pathway in a rat model of central retinal artery occlusion," Invest. Ophthalmol. Vis. Sci. 46(6): 2133-2139.

Zhang et al. (2007) "Imaging the impact of cortical microcirculation on synaptic structure and sensory-evoked hemodynamic responses in vivo," PLoS Biol. 5(5), e119: pp. 1152-1167.

Zhang et al. (2008) "Natural history and histology in a rat model of laser-induced photothrombotic retinal vein occlusion," Curr. Eye Res. 33: 365-376.

Zhang et al. (2015) "In vivo wide-field multispectral scanning laser ophthalmoscopy-optical coherence tomography mouse retinal imager: longitudinal imaging of ganglion cells, microglia, and Müller glia, and mapping of the mouse retinal and choroidal vasculature," J. Biomed. Opt. 20(12): 126005-1-126005-10.

\* cited by examiner

Handheld device to
provide OCT data

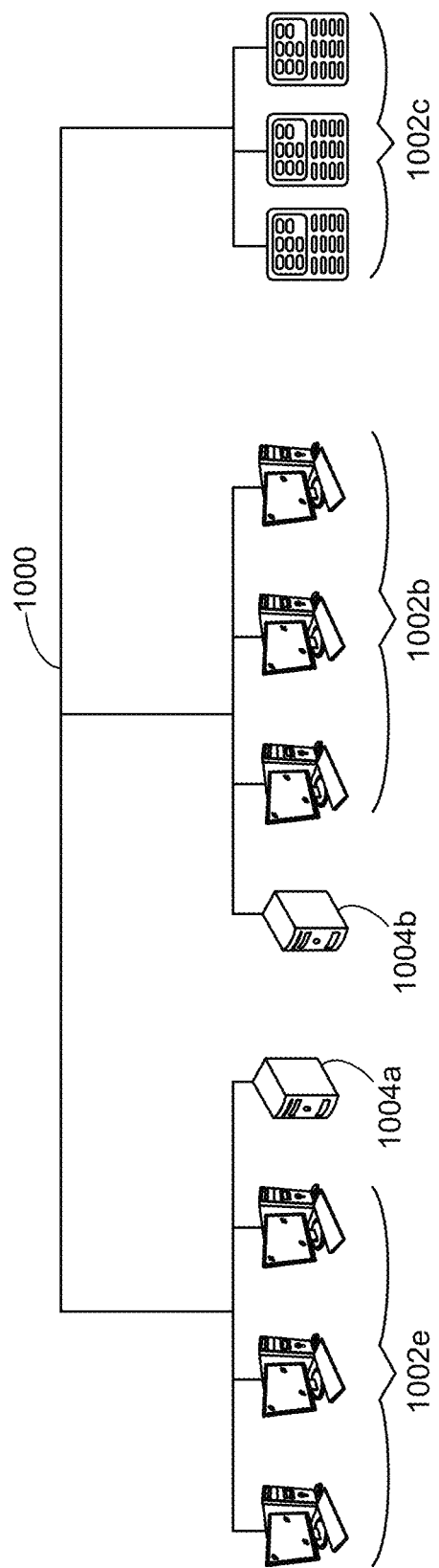

IMAGING-GUIDED CREATING AND MONITORING OF RETINAL VASCULAR OCCLUSIVE DISEASE

CROSS-REFERENCE TO RELATED APPLICATIONS

This patent claims the benefit of U.S. Provisional Application Ser. No. 62/517,341, entitled "Imaging-Guided Creating and Monitoring of Retinal Vascular Occlusive Disease," which was filed on Jun. 9, 2017, and which is hereby incorporated herein by reference in its entirety for all purposes.

STATEMENT REGARDING FEDERALLY SPONSORED RESEARCH FOR DEVELOPMENT

This invention was made with government support under DP3 DK108248, R01 EY026078, R24 EY022883, T32 GM008152, and F30 EY026472 awarded by the National Institutes of Health. The government has certain rights in the invention.

BACKGROUND

Retinal vascular occlusive diseases represent a major form of vision loss worldwide. Retinal vascular occlusive diseases represent the most common cause of visual disability in the elderly population. Two important vascular occlusive diseases are retinal vein occlusions (RVO) and retinal artery occlusions (RAO), with each having different etiologies, pathogenesis, and visual outcomes. Generally speaking, these diseases present with painless, sudden vision loss or blurring in a patient greater than 50 years of age. A unifying feature of these diseases is reduced blood flow, which occurs either in a retinal vein (RVO) or in a retinal artery (RAO). Causes for the ischemia include vessel blockage by either thrombi or emboli, among many others. For RVO, the central vein or a branch thereof can be affected, which are termed central RVO (CRVO) and branch RVO (BRVO), respectively. Similarly, RAO can also be classified into central RAO (CRAO) and branch RAO (BRAO). Importantly, BRVO is the second most common retinal vascular disease after diabetic retinopathy, affecting approximately 16.4 million people worldwide.

BRIEF DESCRIPTION

Certain examples provide an integrated optical coherence tomography (OCT) and scanning laser ophthalmoscope (SLO) apparatus. The example apparatus includes an OCT subsystem to acquire baseline OCT and OCT angiography (OCTA) volumes of a subject without dye before occlusion and subsequent OCT and OCTA volumes of the subject with dye after occlusion. The example apparatus includes an SLO subsystem including a laser controlled to adjust a laser to form a vascular occlusion at a location on a target vessel of the subject. The example apparatus includes a processor to process the OCT and OCTA volumes and feedback from the OCT subsystem and the SLO subsystem to determine a change in three-dimensional vasculature from before the vascular occlusion to after the vascular occlusion.

Certain examples provide a method including acquiring, using an integrated optical coherence tomography (OCT) and scanning laser ophthalmoscope (SLO) apparatus, baseline OCT and OCT angiography (OCTA) volumes of a subject. The example method includes controlling, using the integrated OCT and SLO apparatus, a laser to form a vascular occlusion at a location on a target vessel of the subject, the subject having a photosensitive dye injected. The example method includes acquiring, using the integrated OCT and SLO apparatus, one or more subsequent OCT and OCTA volumes of the subject after the vascular occlusion. The example method includes processing the OCT and OCTA volumes and feedback from the integrated OCT and SLO apparatus to determine a change in three-dimensional vasculature from before the vascular occlusion to after the vascular occlusion.

Certain examples provide at least one computer-readable storage medium including instructions that, when executed, cause at least one processor to at least: generate a location on a target vessel to control a laser in a scanning laser ophthalmoscope (SLO) to form a vascular occlusion at the location; process first data acquired from optical coherence tomography (OCT) and OCT angiography (OCTA) volumes including the target vessel obtained before the vascular occlusion in contrast with second data acquired from OCT and OCTA volumes including the target vessel obtained after the vascular occlusion to determine a change in three-dimensional vasculature from before the vascular occlusion to after the vascular occlusion; and generate a model of a subject including the target vessel based on the first data, the second data, and the change in the three-dimensional vasculature.

BRIEF DESCRIPTION OF THE DRAWINGS

A better understanding of the features and advantages of this disclosure will be obtained by reference to the following detailed description that sets forth illustrative examples, in which the principles of a device of this disclosure are utilized, and the accompanying drawings.

FIGS. 4A-7E show example images and associated measurements obtained using apparatus and methods disclosed and described herein, such as the apparatus of FIGS. 1 and 3 and the methods of FIG. 2A-2B.

FIGS. 8-10 depict example software and computer processor systems on which the systems and methods described and disclosed herein can be implemented.

Figure 1:
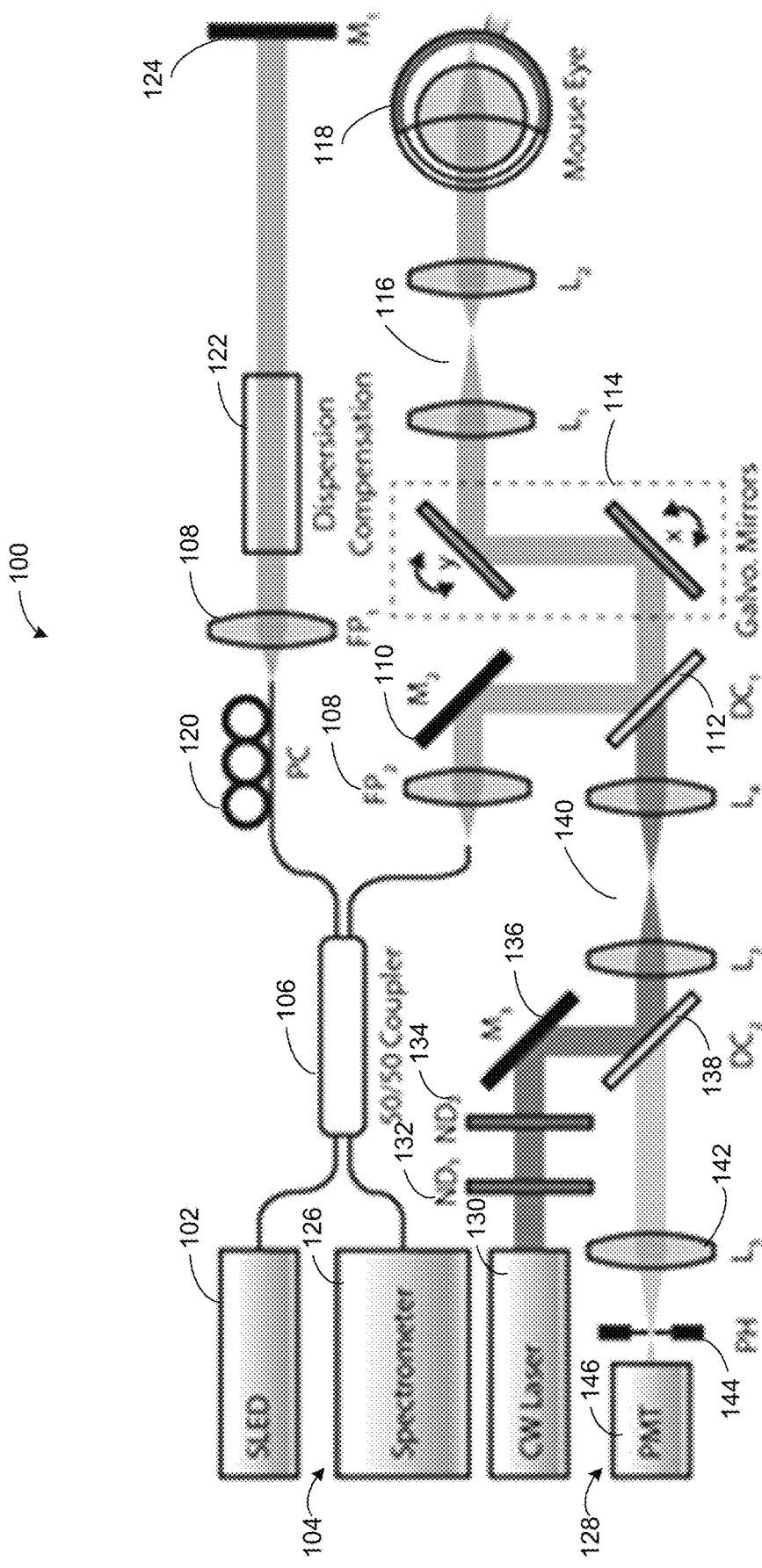
FIG. 1 illustrates an example combined OCT-SLO apparatus.

The following detailed description of certain examples of the present invention will be better understood when read in conjunction with the appended drawings. For the purpose of illustrating the invention, certain examples are shown in the drawings. It should be understood, however, that the present invention is not limited to the arrangements and instrumentality shown in the attached drawings.

DETAILED DESCRIPTION OF THE DISCLOSURE

Terminology

The terminology used herein is for the purpose of describing particular examples only and is not intended to be limiting of a device of this disclosure. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

Several aspects of a device of this disclosure are described above with reference to example applications for illustration. It should be understood that numerous specific details, relationships, and methods are set forth to provide a full understanding of a device. One having ordinary skill in the relevant art, however, will readily recognize that a device can be practiced without one or more of the specific details or with other methods. This disclosure is not limited by the illustrated ordering of acts or events, as some acts may occur in different orders and/or concurrently with other acts or events. Furthermore, not all illustrated acts or events are required to implement a methodology in accordance with this disclosure.

Ranges can be expressed herein as from "about" one particular value, and/or to "about" another particular value. When such a range is expressed, another example includes from the one particular value and/or to the other particular value. Similarly, when values are expressed as approximations, by use of the antecedent "about," it will be understood that the particular value forms another example. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5.

OCT Example Systems and Methods

Optical Coherence Tomography (OCT) is a non-invasive optical imaging technique which produces depth-resolved reflectance imaging of samples through the use of a low coherence interferometer system. OCT imaging allows for three-dimensional (3D) visualization of structures in a variety of biological systems and non-biological systems not easily accessible through other imaging techniques. In some instances, OCT may provide a non-invasive, non-contact means of assessing information without disturbing or injuring a target or sample. In medicine for example, OCT applications have included but are not limited to non-invasive means of diagnosis of diseases in the retina of the eye, interventional cardiology treatment and assessment, and diagnostics of skins lesion for dermatology.

Generally, OCT is used to generate 3D images of various structures, including vessels such as blood vasculature. Previously described methods of OCT provide methods for obtaining structural information directed at acquiring information about the size, shape, topology and physical attributes of the outside structures of vessels. However, information regarding physical and chemical attributes inside vessels and structures can also be useful, yielding more functional and potentially useful information about a system.

The terms "optical coherence tomography" and "OCT" generally refer to an interferometric technique for imaging samples, in some examples, with micrometer lateral resolution. This non-invasive optical tomographic imaging technique is used in variety of medical and industrial applications to provide cross-sectional or 3D images of a target.

The terms "functional OCT" and "fOCT" generally refer to a method of OCT imaging that provides for the acquisition of both structural (e.g., 3D, tomographic and cross-sectional information) and functional information about a target. In some examples, fOCT may be referred to as "visible-OCT" or "vis-OCT." Vis-OCT generally refers to a type of fOCT that includes visible light. fOCT may utilize any method of OCT. Generally, fOCT may be configured with an interferometer, as is the example for many other OCT methods. Light from a light source (for example, a broadband light source) is split (for example, by a beam-splitter) and travels along a sample arm (generally comprising the sample) and a reference arm (generally comprising a mirror). A portion of the light from the sample arm illuminates a target is reflected by the target. Light is also reflected from a mirror in the reference arm. (Light from the test arm and the reference arm is recombined, for example by the beam-splitter.) When the distance travelled by light in the sample arm is within a coherence length of the distance travelled by light in the reference arm, optical interference occurs, which affects the intensity of the recombined light. The intensity of the combined reflected light varies depending on the target properties. Thus, variations for the intensity of the reflectance measured are indications of the physical features or attributes of the target being imaged.

In some examples, the devices, methods and systems of the disclosure may utilize time-domain OCT, where the length of the reference arm can be varied (for example, by moving one or more reference mirrors). The reflectance observed as the reference arm distance changes indicates sample properties at different depths of the sample. In some examples, the length of the sample arm is varied instead of or in addition to the variation of the reference arm length. In some examples, the devices, methods and systems may utilize frequency-domain OCT, where the distance of the reference arm can be fixed, and the reflectance can then be measured at different frequencies. For example, the frequency of light emitted from a light source can be scanned across a range of frequencies or a dispersive element, such as a grating, and a detector array may be used to separate and detect different wavelengths. Fourier analysis can convert the frequency-dependent reflectance properties to distance-dependent reflectance properties, thereby indicating sample properties at different sample depths. In certain examples, OCT can show additional information or data not obtainable from other forms of imaging.

In some examples, the devices, methods and systems of the disclosure may utilize frequency-domain optical coherence tomography, where the reference and sample arms are fixed. Light from a broadband light source including a plurality of wavelengths is reflected from the sample and interfered with light reflected by the reference mirror/s. The optical spectrum of the reflected signal can be obtained. For example, the light may be input to a spectrometer or a spectrograph, comprising, for example, a grating and a detector array that detects the intensity of light at different frequencies.

Fourier analysis may be performed, for example, by a processor, and may convert data corresponding to a plurality of frequencies to that corresponding to a plurality of positions within the sample. Thus, data from a plurality of sample depths can be simultaneously collected without the need for scanning of the reference arm (or sample) arms. Additional details related to frequency domain optical coherence tomography are described in Vakhtin et al., (Vakhtin A B, Kane D J, Wood W R and Peterson K A. "Common-path interferometer for frequency-domain optical coherence tomography," Applied Optics. 42(34), 6953-6958 (2003)) and incorporated by reference herein.

Other methods of performing optical coherence tomography are possible. For example, in some examples of frequency domain optical coherence tomography, the frequency of light emitted from a light source varies in time. Thus, differences in light intensity as a function of time relate to different light frequencies. When a spectrally time-varying light source is used, a detector may detect light intensity as a function of time to obtain optical spectrum of the interference signal. The Fourier transform of the optical spectrum may be employed as described herein. The devices, methods and systems of the disclosure may utilize any method of OCT, including but not limited to spectral domain OCT, Fourier domain OCT, time encoded frequency domain OCT, or swept source OCT, single point OCT, confocal OCT, parallel OCT, or full field OCT as known in the art.

Generally, the term "A-scan" OR "A-line" describes the light reflectivity associated with different sample depths. The term "B-scan" or "B-line" as used herein refers to the use of cross-sectional views of tissues formed by assembly of a plurality of A-scans. In the example of fOCT methods of cancer detection, light reflected by cancerous tissue target is converted into electrical signals and can be used to generate both cross-sectional or 3D structural images and metabolic functional information about the target tissue (such as cancerous growth, lesion, or tumor). In the example of ophthalmology, light reflected by eye tissues is converted into electrical signals and can be used to provide data regarding the 3D structure of tissue in the eye and metabolic activity in the retina. In many examples, including but not limited to cancer detection and ophthalmology, A-scans and B-scans can be used, for example, for differentiating normal and abnormal tissue.

For general methods, an A-scan can generally include data at plurality of depths in a z-axis direction, and a B-scan may include cross-sectional data from a medial border to a lateral border, or (x,y) axis direction. In the example of fOCT of a skin cancer lesion, for example, an A-scan can generally include data from the outer regions of the epidermis of the lesion to the inner regions comprising vasculature, while B-scans can include cross sectional data from one lesion border to another in the (x,y) plane. In ophthalmic instances, an A-scan can generally include data from the cornea to the retina, and a B-scan can include cross-sectional data from a medial border to a lateral border of the eye and from the cornea to the retina. 3D C-scans may be used to generate one or more 3D images by combining a plurality of B-scans in variety of examples.

In the present disclosure, a "target" may indicate any sample, object, or subject suitable for imaging. In some examples, a target may include but is not limited to inanimate material such as metals, alloys, polymers, and minerals as found for industrial applications for OCT and as described herein. In some examples, a target may be animate material, such any suitable living material including but not limited to embryos, seeds, cells, tissues, grafts, blood vessels, organs (e.g., eye/retina, etc.), and/or organisms as would be suitable for medical and agricultural applications for OCT as described herein.

Example Modeling Systems and Methods with Imaging Guidance

Retinal vascular occlusive diseases are a group of disorders which can lead the blindness, especially in the elderly. Producing animal models of these diseases has been extremely cumbersome. Prior techniques to produce the animal models typically involve a skilled operator with extensive training, who has to manually visualize the retina and deliver high-power laser shots to a vessel of interest. In contrast, certain examples provide an imaging-guided approach to producing animal models of diseases. The imaging-guided approach allows easy and precise targeting of a vessel for occlusion, with little training and time. This technology enables the potential for rapid production of the animal model, which in turn facilitates studies on the disease's appearance on imaging and therapeutic targets, for example.

More particularly, two major techniques have been developed to create rodent models of retinal vascular occlusions. In the first technique, the fundus is visualized with a modified slit-lamp biomicroscope using a high-power laser delivery system (~100-200 mW). A skilled operator then manually delivers high energy laser shots to a target retinal vessel until vascular occlusion appears to have occurred. The high-power laser shots may damage the retina, leading to interstitial edema. In turn, the edema eventually compresses the target vessel, resulting in vascular occlusion. In the case of RVOs, the retina appears swollen and pale, and retinal vessels may appear tortuous and white.

In the second technique, a photoreactive dye, such as fluorescein or Rose Bengal (RB), is injected intravenously. Similar to the first technique, high-power laser shots are delivered to a target vessel. When exposed to high-power light, the intravascular RB (or fluorescein) releases singlet oxygen, which, in turn, react with proteins and fatty acids on the blood vessel wall. This oxidation process results in the recruitment of platelets and activation of the coagulation cascade, which altogether lead to the formation of an intravascular thrombus at the targeted site. Compared to the first technique, the second technique creates occlusions which better resemble the pathophysiology of human retinal vascular occlusions. Certain examples improve upon the second technique.

Unfortunately, using a slit-lamp biomicroscope to observe and initiate occlusion has several drawbacks. First, extensive training and expertise are required to maneuver the slit-lamp and deliver the laser shots, especially when dealing with the small dimensions of the mouse eye and the fast clearance of RB from the circulation (~5 minutes). This steep learning curve also introduces variations among different operators. Second, the spot size of the high-power laser on the retina is difficult to control visually; therefore, a large area around the vessel may be illuminated with high-power, resulting in unwanted tissue damage. Finally, the retinal vascular occlusion is not monitored using the direct evidence from examining the blood flow within the vessel. Instead, vascular occlusion is inferred when the retinal vessel, or the surrounding area, appears pale.

Thus, certain examples address the difficulties and shortcomings of these techniques with an integrated imaging and laser occlusion device and associated protocol, which can consistently and precisely produce vascular occlusions with real-time (or substantially real-time given data transmission, processing, and storage latency) monitoring of the occlusion process. Using the device, occlusions can be produced, and vascular changes can be monitored with OCT angiography (OCTA), for example. Additionally, changes in retinal thickness can be quantified over time using layer segmentation performed on OCT volumes, for example.

Certain examples can be applied to production of branch retinal vein occlusions, central retinal vein occlusions, branch retinal artery occlusions, central retinal artery occlusions in animals. Certain examples can be applied to imaging the production of the occlusion in real-time. Certain examples can be applied to imaging the aftermath and longitudinal follow-up of occlusions.

Certain examples reduce training time while increasing consistency among ophthalmology studies and increasing precision when targeting a vessel. Certain examples decrease damage to a retina by focusing light directly onto a vessel of interest. Certain examples provide real-time (or substantially real-time accounting for a light propagation, data processing, data storage, and/or data transmission latency) visualization of clot formation. Certain examples enable monitoring of the retina before and after occlusion.

Certain examples combine optical coherence tomography (OCT), optical coherence tomography angiography (OCTA), and scanning laser ophthalmoscope into an imaging system for a target (e.g., rodents, etc.). Rose Bengal and/or other fluorescein dye can be injected into a subject (e.g., a tail vein of a rodent, etc.). Scanning mirrors of the imaging system can direct a high power laser to a vessel location. The high laser power combined with the Rose Bengal results in clot formation at a specific vessel location. The SLO can evaluate the formation of the clot in real-time and assess the blood flow patterns before and after occlusion. For example, an SLO laser is a high power laser that can be turned from low to high power to form a vascular occlusion in an eye. The OCT system can evaluate the three-dimensional structural changes before and after retinal vascular occlusion in rodents. The OCTA system can evaluate the three-dimensional vasculature before and after occlusion.

In certain examples, an eye model can be generated by: 1) acquiring baseline OCT and OCTA volumes; 2) injecting Rose Bengal and/or other fluorescein; 3) selecting a target vessel for occlusion; 4) acquiring post-occlusion OCT and OCTA volumes, and 5) performing offline OCTA image processing. Thus, OCTA of retinal vascular occlusions produced by imaging-guided laser photocoagulation can be facilitated. Certain examples facilitate real-time (or substantially real-time) clot formation, 3D imaging, angiography, etc., via the imaging-guided OCTA.

Certain examples improve generation of animal models of retinal vascular occlusive disease. These models take time and experience to create and are not well studied. The presently-described device can be used to produce a model quickly to investigate immune response and analyze therapeutic targets, for example.

Example Integrated Imaging and Laser Occlusion Devices and Associated Methods

Certain examples provide a multimodal imaging system to produce laser-induced vascular occlusions with a stain such as RB, etc. Multimodal imaging systems can produce, image, and monitor an animal model. An example multimodal imaging system can include one or more combinations of fundus photography, scanning laser ophthalmoscopy (SLO), autofluorescence imaging, photoacoustic ophthalmoscopy, etc., with optical coherence tomography (OCT). Certain systems can include directed laser delivery, which enables consistent reproduction of animal models with reduced training time. For ophthalmology, for example, laser-induced choroidal neovascularization (CNV) provides a model of wet age-related macular degeneration, which can be difficult to produce due to inconsistent laser burns administered by a slit-lamp protocol. Certain examples address this difficulty and provide a solution to produce animal models of retinal vascular occlusive diseases.

Certain examples provide visualization of three-dimensional (3D) retinal structure before and after vascular occlusion and visualization of retinal microvasculature before and after vascular occlusion. Certain examples precisely direct actinic laser light to a specific vessel location with minimal laser power to visualize vascular occlusions in real-time. These capabilities are provided by an integrated optical coherence tomography (OCT) and fluorescent scanning laser ophthalmoscope (SLO) system. The OCT sub-system performs high-resolution cross-sectional imaging of the retina and enables OCT angiography, which can obtain high-contrast images of microvasculature. The SLO sub-system performs RB angiograms, ensuring RB within the retinal vasculature. Subsequently, the SLO also directs actinic light precisely to a selected vessel location, while also visualizing the occlusion process in real-time. Ultimately, using the multimodal imaging system, BRVO, CRVO, and BRAO patterns can be demonstrated in a murine retina, for example.

FIG. 1 illustrates an example combined OCT-SLO apparatus 100. The example OCT-SLO apparatus 100 includes a light source 102 in a spectral-domain OCT (SD-OCT) sub-system 104. The example light source 102 can include a superluminescent light emitting diode (SLED) (e.g., IPSDW0825C-0314, InPhenix) with a center wavelength of 840 nm and a bandwidth of 95 nm (e.g., full width at half maximum), for example. A 50/50 fiber coupler 106 (e.g., FUSED-22-850, OZ Optics) collects light from the SLED and/or other light source 102 and splits the light into sample and reference arms. The beam at each arm is collimated by an aspheric fiberport 108 (e.g., FP1 and FP2; PAF-X-11-PC-B, Thorlabs). The sample arm beam is reflected by a mirror 110 and then combined with the SLO illumination beam by a short pass dichroic mirror 112 (e.g., DC1; FF746, Semrock). X-y scanning galvanometer mirrors 114 (e.g., QS-7, Nutfield Technology) deflect a combined beam for raster scanning. A 5/1 Keplerian telescope 116 including two achromatic lenses (e.g., L1 and L2; VIS-NIR coated, 75 mm and 15 mm focal lengths, Edmund Optics) create a point conjugate to the scanning mirrors 114, which is aligned at a pupil plane of a target 118 such a mouse eye, human eye, etc. The reference arm beam passes through a polarization controller 120 before the fiberport 108 and is reflected back by a silver mirror (M1) 124 after passing through a plurality of glass plates 122 (e.g., BK7 glass plates), which are used for dispersion compensation. The back-reflected sample beam recombines and interferes with the backscattered light from the sample. A spectrometer 126 detects and digitizes the interference signals.

An SLO and laser occlusion sub-system 128 uses a continuous wave (CW) diode-pumped solid-state laser 130 (e.g., 532 nm, 100 mW). For coarse control of the laser power, the SLO illumination beam passes through a manual neutral density filter wheel 132 (e.g., ND1; Thorlabs, FW1AND). For fine control of the laser power, the SLO illumination also passes through a continuous neutral density filter wheel 134 (e.g., ND2; Thorlabs, NDC-50C-2M-A). A mirror 136 and a long pass dichroic mirror 138 (e.g., DC2; FF560, Semrock) serve to reflect the illumination beam and pass RB fluorescence (e.g., peak emission: 571 nm). A Keplerian telescope 140 (L3 and L4) resizes the illumination beam and passes the illumination beam to the dichroic mirror 112 (DC1) shared with the OCT sub-system 102. The SLO and OCT illumination beams are coaxially aligned, such that they share the same relay optics 116 and scanning mirrors 114 to reach the subject's 118 pupil plane. After passing through the long pass dichroic mirror (DC2) 138, the RB fluorescence is focused by a lens (L5) 142 and spatially filtered by a pinhole 144 (e.g., PH; 50 microns, Thorlabs). A photomultiplier tube 146 (e.g., PMT; Hamamatsu) captures the fluorescence signal, which is converted from current to voltage and digitally acquired.

Example Scanning Protocols for OCT and SLO Imaging

Both OCT 104 and SLO 128 use raster scanning to acquire images. The galvanometer mirrors 114 deflect the illumination beams, which changed the angle of the illumination beam at the pupil plane, to achieve raster scanning of the retina. OCT detects backscattered photons by low-coherence interferometry, while SLO collects RB fluorescence in retinal blood flow. The imaging systems 104, 128 can be controlled such as using Labview software (e.g., 2015 SP1, 64-bit, National Instruments).

Example OCT imaging protocols

Certain examples provide a plurality of OCT imaging protocols including a preview OCT protocol and a high-density OCT/OCTA protocol. In one example, an A-line acquisition rate for both protocols is set to 70 kHz; a scanning area is 2.5 mm×2.5 mm; and an illumination at the pupil plane is 1 mW. The preview OCT protocol allows quick positioning of the target (e.g., the eye) as well as a preview of image quality. An example image includes 64 B-scans with 128 A-lines in each B-scan. To preview a volumetric OCT image in real-time, a CUDA C program can be generated, and CUDA-accelerated parallel functions can be executed on a graphics card (e.g., GeForce GTX 750Ti, NVIDIA Corporation). The real-time preview has a frame rate of 5.9 frames per second (FPS), which may be limited by the galvanometer mirrors 114. En face images can be generated by calculating a maximum amplitude projection (MAP) along an axial direction of the 3D volume data. Alongside the MAP, a selected B-scan from the 3D volume can be displayed, helping an operator to better position the target (e.g., the eye).

Once the initial alignment is completed, images can be captured using a high-density OCT/OCTA protocol, such as recording 400×512 A-lines per image. Additionally, at each of 512 B-scan positions, additional five co-localized B-scans can be sequentially acquired for OCTA, making the total acquired B-scans equal to 2560, for example (e.g., with a total acquisition time for this protocol of 20.5 seconds, etc.). Using the OCT/OCTA protocol, the data can be processed offline such as using a MATLAB program. Due to a limited field of view in each acquisition, the high-density protocol can be repeated at different fundus locations, and the resulting images can be montaged and/or otherwise combined.

In certain examples, OCT images from the high-density protocol are constructed from an average of the five repeated B-scans. An OCT angiogram can be constructed from the five repeated B-scans using an amplitude-based OCTA algorithm, for example. B-scans are correlated and shifted to adjust for global and lateral phase fluctuations. For visualization, the 3D OCTA volumes can be converted to depth color-coded MAP, for example. Some or all OCTA images can be automatically montaged together such as using i2k Retina software (DualAlign LLC, Clifton Park, N.Y.), Adobe Photoshop (Creative Cloud, Adobe Systems Incorporated, San Jose, Calif.), etc.

Example SLO Imaging

In certain examples, the SLO sub-system 128 also provides two imaging protocols: an angiography protocol and an actinic protocol. The angiography protocol obtains RB fluorescence angiograms of retinal vessels, for example. In an example, a scanning area is 2.5 mm by 2.5 mm (same as OCT) with a scanning density of 128×128 pixels; illumination power at the target (e.g., pupil) is 400 µW; and acquisition rate is 1.9 FPS. The actinic protocol delivers high-power actinic light to a target vessel. By manipulating a deflection angle of the x-y scanning galvanometers 114, the scanning area can be reduced and shifted to cover only the diameter of the target vessel. In an example, the scanning density is 64×64 pixels; the illumination power at the pupil is 25 mW to 35 mW; and the acquisition rate is 5.9 FPS.

Example Retinal Vascular Occlusion Protocol

Figure 2A:
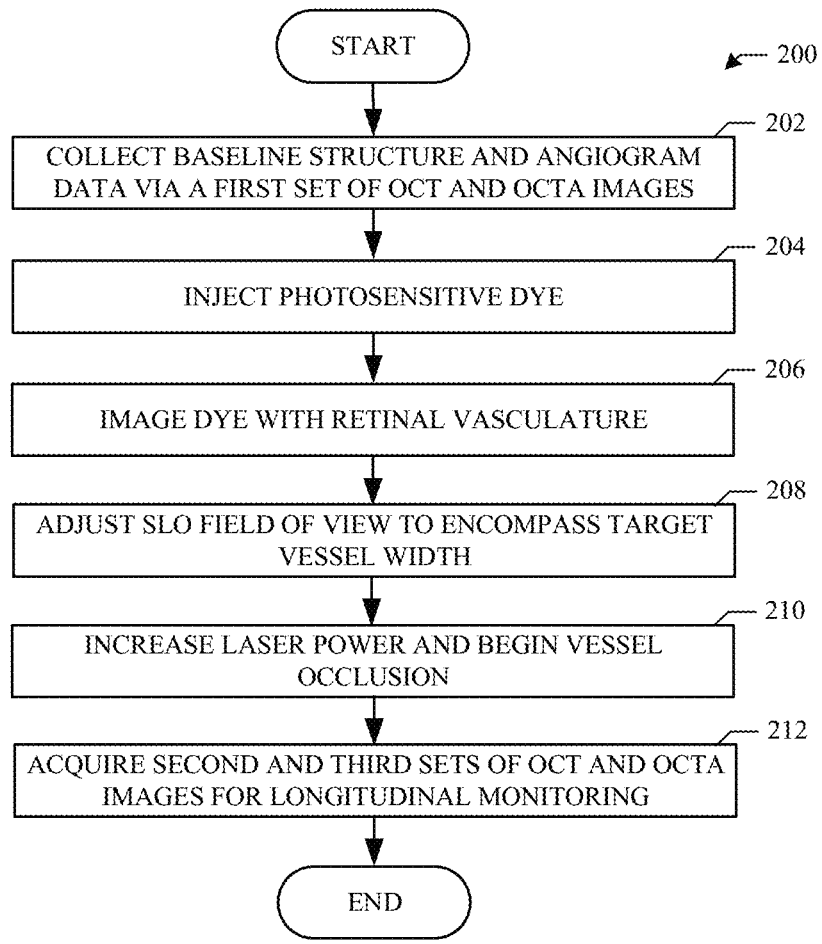
FIGS. 2A-2B illustrate flow diagrams of example methods of retinal vascular occlusion protocol analysis to generate and process retinal images.

FIG. 2A illustrates a flow chart for an example method 200 of retinal vascular occlusion protocol analysis to generate and process retinal images. At block 202, a target is imaged using OCT and OCTA to collect baseline structure and angiogram data. For example, after anesthesia induction, a subject is imaged using OCT and OCTA. At block 204, a photosensitive dye solution (e.g., Rose Bengal, etc.) is injected (e.g., into a lateral tail vein of a subject including the target, etc.). At block 206, the dye is imaged within the retinal vasculature.

At block 208, to perform vascular occlusion, a field of view of the SLO system is adjusted to encompass a width of the target vessel. Then, at block 210, the laser power of the SLO system is increased (e.g., to ~20 mW, etc.) to begin occluding the target vessel. Using SLO, the occlusion process can be monitored in real time (e.g., taking <10 seconds, etc.). At block 212, for longitudinal monitoring, OCT and OCTA images are acquired following the occlusion and again one day after occlusion.

Figure 2B:
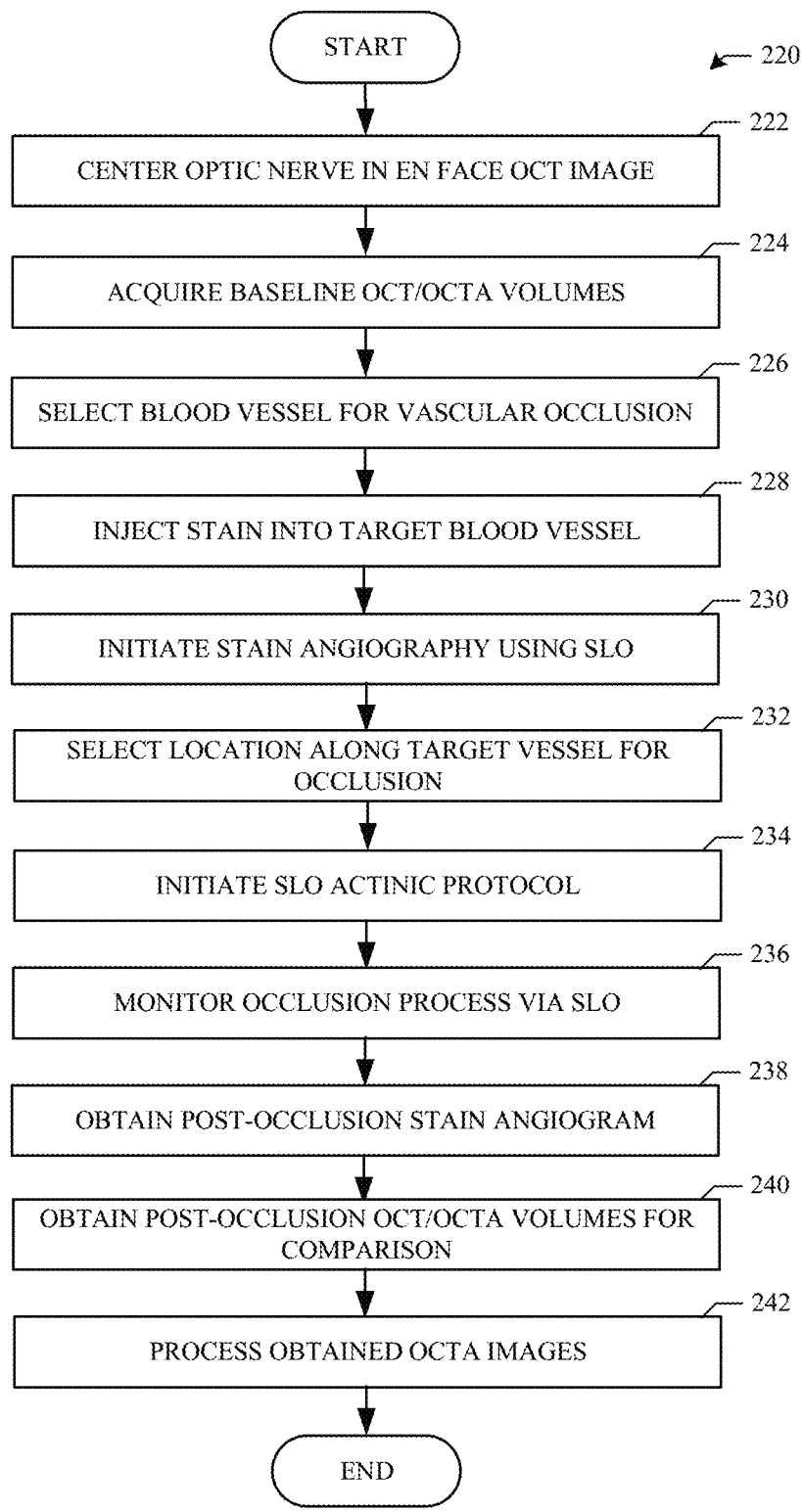

FIG. 2B illustrates a flow chart for a more detailed example method 220 of retinal vascular occlusion protocol analysis to generate and process retinal images. At block 222, an optic nerve of a target eye is centered in an OCT en face image. For example, a preview protocol can be used to center the optic nerve head on the OCT en face image. At block 224, one or more baseline OCT/OCTA volumes are acquired using a high-density protocol. At block 226, a blood vessel is selected for vascular occlusion. For example, using the en face preview, an artery or vein is selected for vascular occlusion. Arteries can be distinguished from veins on en face OCT by their smaller diameter and more frequent branch points in the nerve fiber layer.

At block 228, a stain such as RB, etc., is injected into the target blood vessel. For example, RB (e.g., Sigma Aldrich, Milwaukee, Wis.) is prepared in physiological saline (e.g., 5 mg/ml of saline) and injected (e.g., 0.2 ml) into a lateral tail vein. RB is selected, for example, over fluorescein because of its higher quantum yield (~25×) for producing reactive single oxygen. At block 230, after stain injection, stain angiography (e.g., RB angiography, etc.) is initiated using the SLO angiography imaging protocol, enabling real-time visualization of the stain in the retinal vasculature.

At block 232, a location along the target vessel is selected for occlusion. For example, a distance from the optic nerve head (ONH) may correlate with severity of the vascular occlusion. Specifically, vein occlusions close to the ONH tend to result in a CRVO pattern, while vein occlusions farther away from the ONH result in a BRVO pattern. Such occurrence can influence and/or otherwise help determine selection of the target location for retinal vascular occlusion.

Once the occlusion site is determined, at block 234, an SLO actinic protocol is initiated. Parameters of the protocol can be adjusted prior to and/or during the initiation. For example, a scanning area is reduced to span the vessel diameter and laser power is increased to 25 mW by adjusting controllable neutral density (ND) filters 132, 134.

At block 236, the occlusion process is monitored using SLO. For example, an output or side effect of the occlusion process can be monitored and analyzed to determine an outcome of the occlusion. For example, if the occlusion is successful, an intravascular fluorescence signal will dramatically fall within several seconds. If the vessel appears only partially occluded, the laser power can be increased up to a maximum of 35 mW, for example, to finish the occlusion process. Previous techniques to produce vascular occlusions used laser powers of 100-200 mW. Using OCT, these laser powers often lead to vessel hemorrhage, rupture of Bruch's membrane, or severe edema immediately following laser delivery. Therefore, certain examples instead reduce the laser power to 25-35 mW to minimize these effects.

At block 238, after completing the vascular occlusion, SLO illumination power is reduced (e.g., to 400 μW), and a post-occlusion stain (e.g., RB) angiogram is obtained (e.g., using an SLO angiography protocol). At block 240, post-occlusion OCT/OCTA volumes are collected for comparison with baseline images (e.g., using a high-density OCT imaging protocol). At block 242, obtained OCTA images are processed offline. For example, obtained OCTA images are processed to analyze the occlusion, model the vessel and/or retina targeted in the imaging to evaluate 3D structural changes in the eye before and after retinal vascular occlusion.

Figure 3:
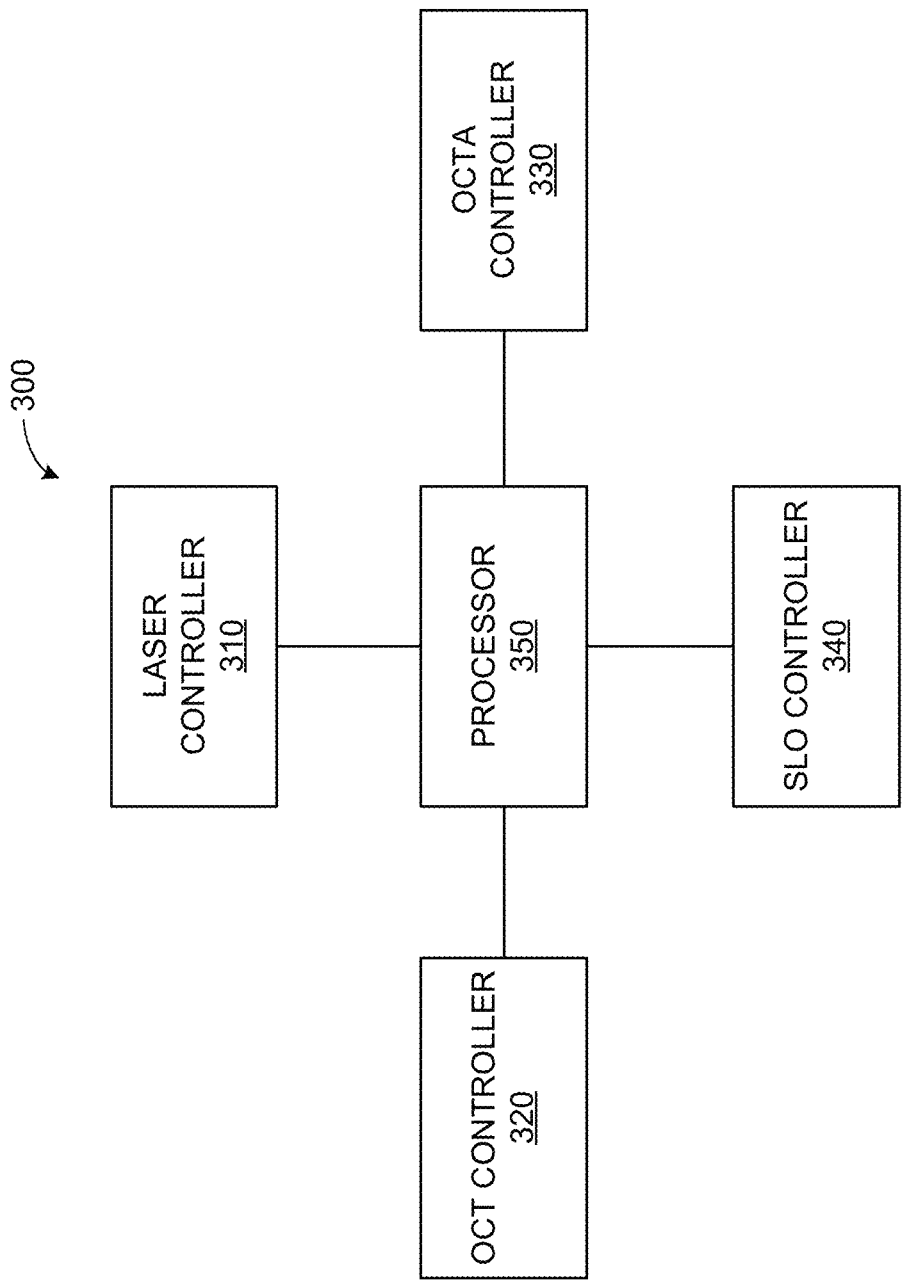
FIG. 3 illustrates an example processing and control system to drive the OCT-SLO apparatus of FIG. 1 to execute the methods of FIG. 2A-2B.

FIG. 3 illustrates an example processing and control system 300 to drive the example OCT-SLO apparatus 100 of FIG. 1 to execute the example methods of FIGS. 2A-2B. The example system 300 includes a laser controller 310, an OCT controller 320, an OCTA controller 330, and an SLO controller 340 communicating with a data processor 350. The example system 300 can be implemented in the one or more subsystems 104, 128 and/or computing device(s) described in one or more of FIGS. 8-10 below, for example. The OCT controller 320 controls the OCT subsystem 104 to perform optical coherence tomography (OCT). The OCTA controller 330 controls the OCT subsystem 104 to perform optical coherence tomography angiography (OCTA). The SLO controller 340 controls the scanning laser ophthalmoscope (SLO) to facilitate and monitor vessel occlusion. The laser controller 310 controls the scanning mirrors 114 to direct the high-power laser 130 to a vessel location specified by the processor 350, which processes OCT and OCTA data from the OCT controller 320 and the OCTA controller 330, respectively. The laser performs vessel occlusion at the location. The processor 350 processes data from the controllers 310-340 to determine dosage, direct mirrors, evaluate clot formation, assess blood flow patterns, evaluate three-dimensional vasculature and associated three-dimensional structural changes before and after retinal vascular occlusion in rodents, etc., to improve model generation/production, model analysis, therapeutic target analysis, and immune response investigation, etc.

FIGS. 4A-4G illustrate example results of producing and analyzing retinal vascular occlusions in target eyes (e.g., a branched retinal vein occlusion, etc.). For example, as shown in the example of FIGS. 4A-4G, a BRVO pattern can be created at a 10 o'clock vein in a target eye. To increase a probability of creating a BRVO pattern, a vessel location greater than four ONH diameters away from the ONH can be targeted. To aid this process, the eye can be aligned, using the preview OCT protocol for guidance, such that the ONH is at the bottom right corner of the field of view (FOV). This alignment places a longer length of the vein within the FOV, enabling selection of an appropriate target location away from the ONH. Next, a pre-occlusion baseline OCTA image, showing the vein of interest, v, is acquired (e.g., FIG. 4A). A stain, such as RB, is administered via a tail vessel injection, and a co-localized pre-occlusion RB angiogram is acquired (e.g., FIG. 4A) using the SLO angiography protocol. RB and/or other stain can be seen flowing with the retinal arteries and veins. A specific location on the vein can be selected/determined for occlusion, indicated by the red box in FIG. 4A.

Figures 4A, 4B, 4C, 4D, 4E, 4F, 4G:
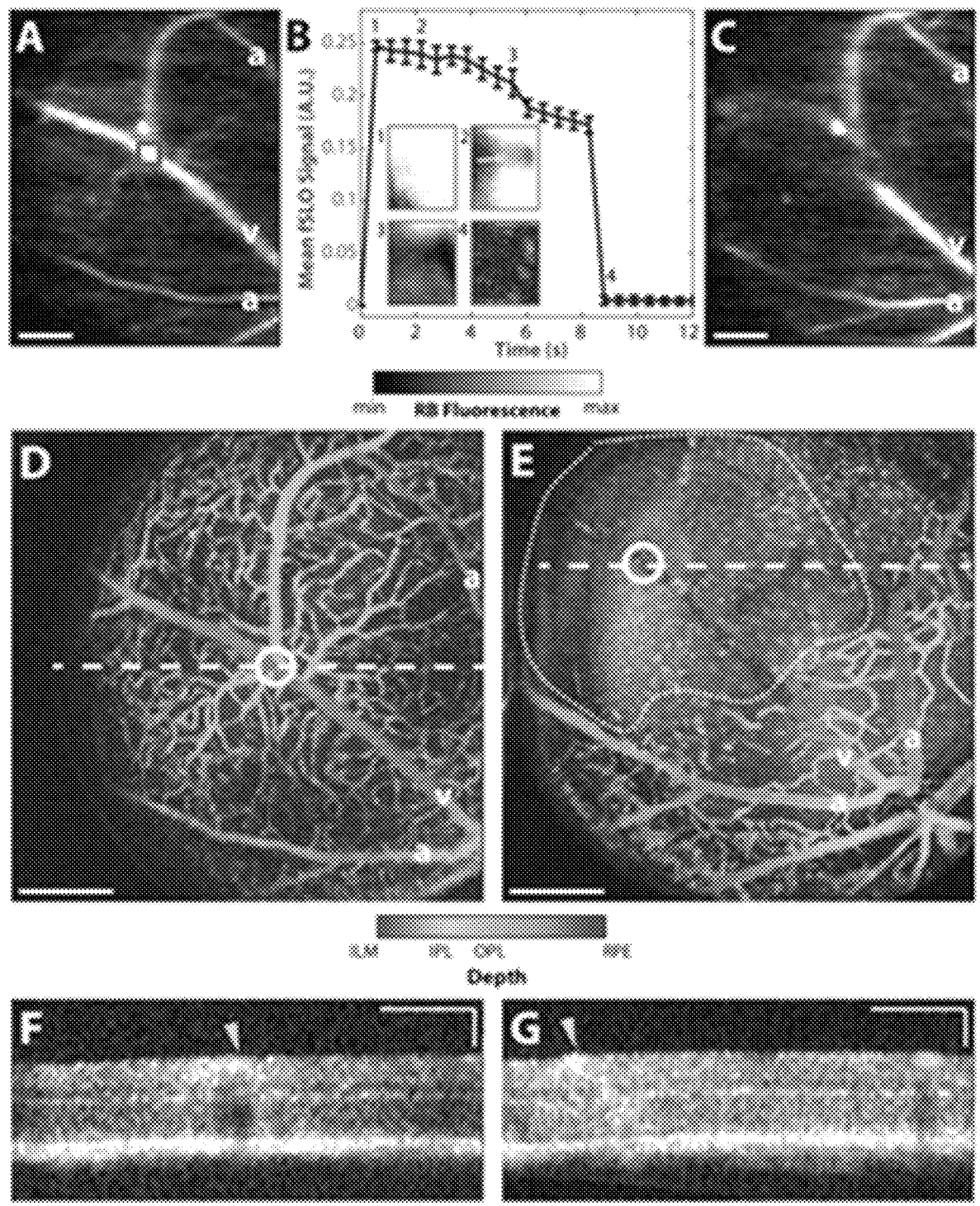

To begin the occlusion procedure (e.g., actinic protocol), the SLO FOV is decreased until the target vein spanned the FOV. Continuous SLO scanning at high laser power (e.g., 25 mW) can then be initiated. From the collected SLO images, a mean RB fluorescence signal versus time can be calculated, as shown in the example of FIG. 4B. Four selected frames of the vessel from an example experiment (including a 12 second occlusion procedure) are shown as insets in FIG. 4B, rectangle frames 1-4. Insets 1 to 4 show frames at points 1 to 4 on a curve with a laser power of 25 mW at the pupil of the target eye.

Frame 1 shows a first acquired SLO image, in which the vessel spans most of the FOV. Frame 2, captured at two seconds, shows a diminished SLO signal near the vessel wall (indicated by an arrow), which represents a nidus for platelet aggregation. By six seconds, Frame 3 shows that RB fluorescence within the FOV is diminishing, which implies decreasing intravascular blood flow. At nine seconds, Frame 4 illustrates that the RB SLO signal diminishes abruptly, which indicates that blood flow is completely stopped at the target site. In certain examples to help ensure stable thrombus formation, high-power scanning can continue for an additional time (e.g., an additional 3 seconds, etc.) after observing diminished intravascular RB SLO signal before the high-power scanning is shut off.

Thus, FIG. 4A illustrates an example pre-occlusion RB angiogram, and the red box indicates a scanning area for occlusion. FIG. 4B shows a mean RB fluorescence signal during occlusion corresponding to the red box in FIG. 4A. FIG. 4C shows an example post-occlusion RB angiogram.

Returning to the SLO angiography protocol (FIG. 4C) reveals vessel discontinuity at the target location and absence of RB fluorescence upstream of the occlusion site, indicating a successful occlusion. Moreover, co-localized post-occlusion OCTA shows diminished OCTA signal within the target vein (FIG. 4D), which also indicates reduced blood flow. Comparing the SLO image with OCTA image, OCTA shows higher contrast and more details of the deeper capillary network. A striking difference between the pre-occlusion and post-occlusion OCTA images is an area of capillary non-perfusion in a sector surrounding the occluded vein (highlighted by a dashed region in the example of FIG. 4E). Pre-occlusion cross-sectional OCT reveals intact retinal layers and a vessel shadow corresponding to the target vessel (FIG. 4F), for example. After the occlusion, the vessel shadow disappears, indicating less absorption by hemoglobin from the reduced blood flow (FIG. 4G). The Bruch's membrane and retinal pigment epithelium (RPE) are intact, no evidence of retinal edema or swelling is discovered, and retinal layers are shown to be intact even in the areas with capillary non-perfusion on OCTA.

Thus, FIGS. 4F and 4G illustrate a pre-occlusion OCT B-scan (at the dashed line in the example pre-occlusion retinal vein OCTA of FIG. 4D, with the solid circle indicating a site of occlusion) and a post-occlusion OCT B-scan (at the dashed lined in the post-occlusion OCTA of FIG. 4E, with the solid circle indicating a site of occlusion), respectively. Dashed regions indicate areas of capillary of non-perfusion. Arrows in FIGS. 4F and 4G indicate vessel location. Horizontal scale bars are 500 μm, and vertical scale bars are 100 μm, with "a" indicating an artery and "v" indicating a vein, for example.

Figures 5A, 5B, 5C, 5D, 5E, 5F, 5G, 5H:
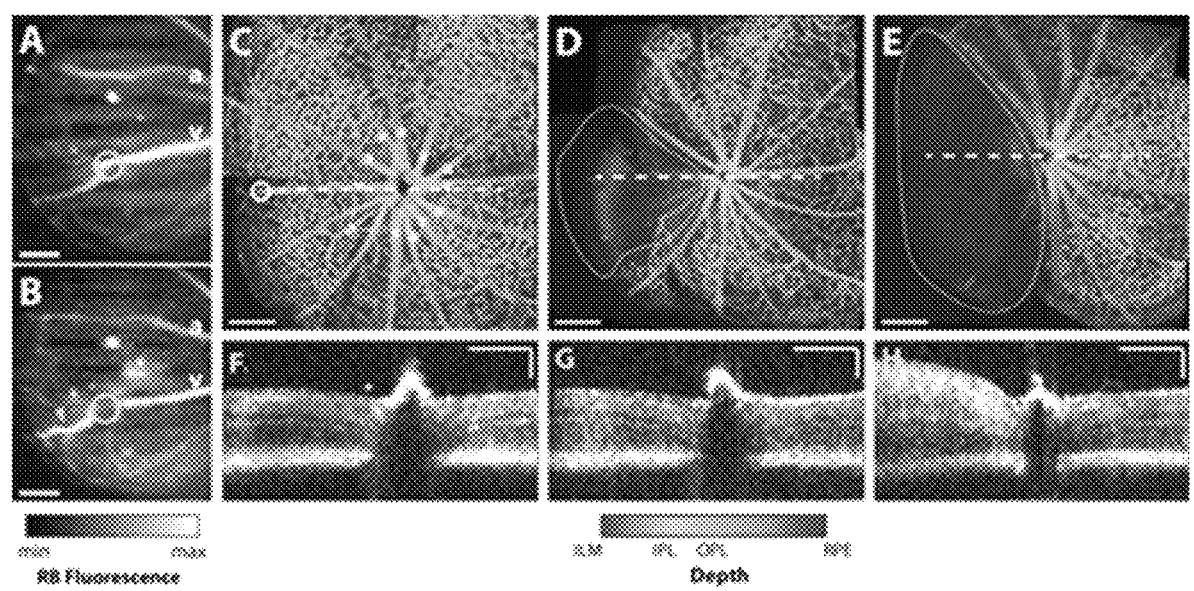

FIGS. 5A-5H illustrate another example in which retinal microvasculature is monitored before and after a BRVO occlusion. In the example, a BRVO is created at the 9 o'clock position, indicated by circles on pre-occlusion and post-occlusion RB angiograms, FIGS. 5A and 5B, respectively. The post-occlusion RB angiogram of FIG. 5B shows increased dilation and tortuosity in the vein before reaching the occlusion site (indicated by an arrow). Additionally, vascular leakage of the RB dye can be observed in the peripheral area (indicated by an arrow). Pre-occlusion (FIG. 5C), post-occlusion (FIG. 5D) and day 1 (FIG. 5E) OCTA montages can be performed. The montages include nine images and covered a larger FOV of approximately 3.5 mm². In the pre-occlusion depth-colored OCTA of FIG. 5C, three healthy vascular networks can be seen: one near the inner limiting membrane (ILM), a second near the inner plexiform layer (IPL), and a third near the outer plexiform layer (OPL). Arteries (a) and veins (v) are labeled and alternate in a retinal pattern. The BRVO location is denoted by a solid circle at the 9 o' clock position.

A dashed region in FIG. 5D shows a sectorial area of capillary non-perfusion associated with the vein occlusion. At day 1, the area of capillary non-perfusion enlarges but stops at the nearest adjacent veins (illustrated by a dashed region in FIG. 5E). This progression of capillary non-perfusion can be observed in both monkey and rat models of BRVO. Slow blood flow may predispose to increased clot formation in the capillary bed, and the interstitial edema may create enough interstitial pressure to close capillaries, for example.

In some examples, BRVO models observe interstitial edema and increased retinal thickness by day 3 post-occlusion. For example, a pre-occlusion OCT B-scan through the ONH shows normal intact retinal layers (FIG. 5F). On the post-occlusion B-scan (FIG. 5G), the retinal layers are still distinguishable on both the sides of the ONH. On day 1, the OCT B-scan shows evident increase in retinal thickness on the side of the retina with the occlusion (FIG. 5H). On the side with occlusion, increased scattering can be observed in the GCL, IPL, and INL layers, and the retinal layer boundaries become hard to distinguish. The retinal layers on the side without occlusion appear intact. In an example, retinal thickness measurements on the side of the occlusion are 265 µm, 273 µm, and 389 µm pre-occlusion, post-occlusion, and day 1 post-occlusion, respectively. In the example, on the opposing side, retinal thickness measurements are 257 µm, 250 µm, and 266 µm pre-occlusion, post-occlusion, and day 1 post-occlusion, respectively. In the example, measurements are performed at a radial distance of 800 µm from the ONH.

Thus, FIGS. 5C-5E show example montages of OCTA images before (FIG. 5C) and after (FIGS. 5D-5E) vein occlusion. Dotted regions in FIGS. 5B-5C denote areas of capillary non-perfusion. FIGS. 5F-5H show example OCT B-scans at the ONH before, after, and at day 1 for a vein occlusion. Dashed lines in FIGS. 5C, 5D, and 5E denote the B-scan position for FIGS. 5F, 5G, and 5H, respectively. In the example, horizontal scale bars are 500 µm, and vertical scale bars are 100 µm.

Figures 6A, 6B, 6C, 6D, 6E, 6F, 6G, 6H, 6I:
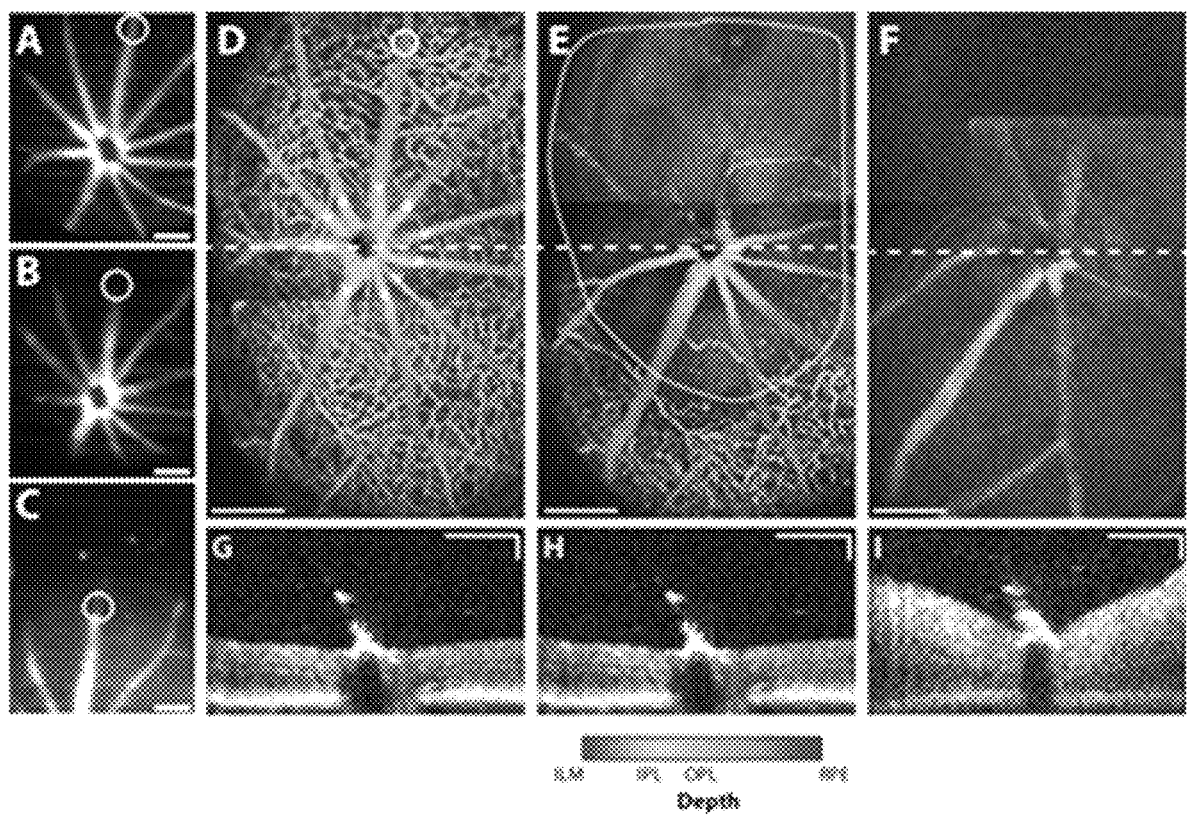

Certain examples produce CRVO patterns of occlusion. For example, a 12 o'clock retinal vein can be targeted at a location approximately 4 ONH diameters away from the ONH to produce CRVO occlusion pattern(s). CRVO patterns are more likely when the target location along the vessel is positioned more proximal to the ONH, for example. FIG. 6A shows an example pre-occlusion RB angiogram for longitudinal OCTA of central vein occlusion with the target location for an occlusion site indicated by a circle. FIGS. 6B and 6C show example post-occlusion RB angiograms. FIG. 6C depicts a post-occlusion RB angiogram positioned away from ONH, for example. In the examples of FIGS. 6B-6C, RB flow is only observed past the occlusion site. The baseline OCTA image shows a healthy adult vascular network (e.g., in the montage of three pre-occlusion OCTA images of FIG. 6D, with "a" labeling arteries and "v" labeling veins and a solid circle showing a target site for vessel occlusion). However, unlike the BRVO-like post-occlusion OCTA montages, a CRVO-like post-occlusion OCTA shows widespread capillary non-perfusion extending beyond adjacent retinal veins (FIG. 6E, which shows a montage of three post-occlusion OCTA images with a dotted region denoting an area of capillary non-perfusion). On day 1, the capillary networks are markedly absent on OCTA, as shown in the montage of 3 OCTA images in FIG. 6F. Corresponding OCT B-scans pre-occlusion for each point in time are shown in FIGS. 6G-6I (corresponding to the dashed lines in FIGS. 6D-6F, respectively, with horizontal scale bars of 500 µm and vertical scale bars of 100 µm). The pre-occlusion and post-occlusion OCT B-scans show intact retinal layers on both sides of the ONH. On day 1 post-occlusion, however, the retinal layer boundaries are obscured, and increased scattering is found throughout the inner retinal layers. Diffuse swelling of the retina is observed on day 1 (FIG. 6I), which differed from the BRVO pattern in FIGS. 5A-5H. The pre-occlusion retinal thickness measurements are 257 µm nasally and 246 µm temporally, for example. The post-occlusion retinal thickness measurements are 273 µm nasally and 250 µm temporally, for example. The retinal thickness measurements on day 1 are 524 µm nasally and 514 µm temporally, for example.

Figures 7A, 7B, 7C, 7D, 7E:
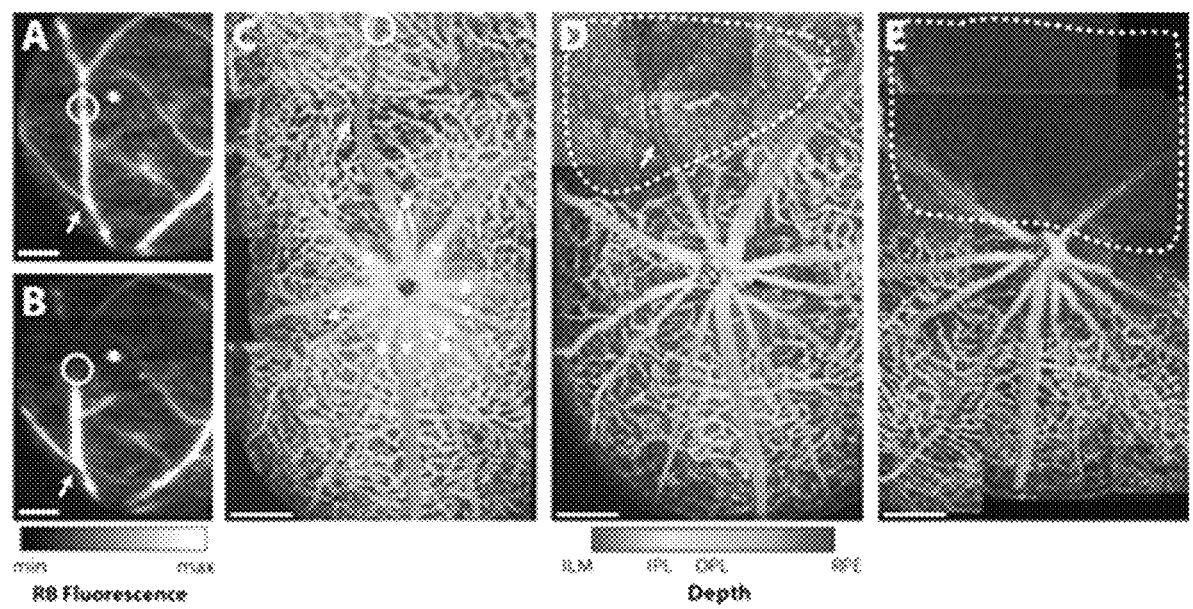

The example of FIGS. 7A-7E illustrates that the presently disclosed imaging-guided vascular occlusion technique can also produce animal models of artery occlusive disease. For example, FIG. 7A shows a pre-occlusion RB angiogram for longitudinal OCTA of a branched artery occlusion with a target location marked by a circle. An arrow indicates a branch point of the arterial tree. FIG. 7B shows a post-occlusion RB angiogram. There was limited flow past the occlusion site. In pre-occlusion OCTA, shown in the montage of three pre-occlusion OCTA images of FIG. 7C, the solid circle indicates the target site of occlusion on an artery at the 12 o'clock position. In the post-occlusion OCTA, shown in the montage of 3 post-occlusion OCTA images of FIG. 7D, a sector of non-perfusion is observed, similar to the vein occlusions shown previously. The dashed region denotes an area of capillary non-perfusion, and the solid arrow indicates an arterial branch point. The arrows on FIGS. 7A-7D highlight a bifurcation of the retinal artery. Since the artery occlusion is positioned past the bifurcation, one of the branches has a diminished OCTA signal, while the other branch continues to have OCTA signal, post-occlusion, which is expected for arterial blood flow. On day 1, as illustrated in FIG. 7E, the OCTA montage of three images shows that region of non-perfusion increased in size, extending to the next adjacent artery (FIG. 7C). In the example of FIG. 7E, the dashed region denotes an area of capillary non-perfusion with a scale bar of 500 µm.

Thus, certain examples provide an imaging system and associated protocol to generate precise retinal occlusions in the murine inner retina (see, e.g., FIGS. 1-2). Certain examples provide SLO guidance to produce retinal vascular occlusions for target studies. To target a vessel for occlusion, SLO is used to help ensure that RB fluorescence is observable within the retinal vasculature. After precisely choosing a target vessel location, the same SLO system is used at a higher laser power to deliver actinic light to the intravascular RB (see, e.g., FIGS. 3A-G). Using this imaging system and occlusion protocol, BRVO patterns (see, e.g., FIGS. 4A-H), CRVO patterns (FIGS. 5A-I), and BRAO patterns (FIGS. 6A-E) in a target retina.

Thus, certain examples provide characterization of retinal occlusions with OCT and OCTA. Acquired OCT volumes enable analysis of retinal edema associated with vascular occlusion. Whereas previous studies have used fluorescein angiography (FA) to study retinal vascular occlusions, certain examples use OCTA to monitor longitudinal changes in the retinal microvasculature, pre-occlusion, immediately post-occlusion, and on day 1 post-occlusion. Unlike FA, OCTA provides 3D images of the vascular network, enabling certain examples to provide a depth color map on en face OCTA montages. Additionally, unlike FA, no contrast agent is required to obtain the angiograms with OCTA, which was extremely desirable for longitudinal monitoring. Moreover, FA has difficulty visualizing the complete deep vascular network compared to OCTA. With OCTA, changes in capillary non-perfusion cases of BRVO, CRVO, and BRAO can be monitored.

Traditionally, creating retinal occlusions has depended primarily upon a slit-lamp biomicroscope. In contrast, certain examples provide a multimodal imaging system to produce retinal occlusions in models (e.g., animal models, human models, etc.) and provides several advantages over using a slit-lamp biomicroscope. First, the multimodal imaging system is easy to use and requires little training to perform the procedure, other than learning how to perform tail injections. Second, the SLO enables the verification of RB within the retinal vessels of the eye. Since RB has a short half-life in the bloodstream of approximately 5 minutes, it is important to verify that RB is within the target retinal vessel. Third, instead of relying on non-specific signs of occlusion (e.g., whitening of the vein) to determine when vascular occlusion occurs, SLO enables monitoring of the thrombus formation in real time. The real-time monitoring allows the operator to remove the high-power illumination after the occlusion is observed, which prevents excess laser dosage to the animal eye. On the other hand, real-time monitoring with SLO also enables the operator to tell if the occlusion is partially formed. At that point, the operator can choose to increase the illuminating laser power to ensure the full formation of the occlusion. Finally, compared with the slit-lamp biomicroscope, the spot size on the retina is better controlled in SLO because the same spot size used for imaging is also used to perform the occlusion. This makes the actinic laser delivery much more precise and minimizes damage to the surrounding retina.

Thus, certain examples provide an OCT and SLO based retinal vascular occlusion system. Such a system integrates imaging and laser occlusion with near-infrared optical coherence tomography (OCT), OCT angiography (OCTA), and fluorescent scanning laser ophthalmoscopy (SLO) with a high-power laser to induce the occlusion. Using SLO combined with OCT angiography, artery and vein occlusions can be longitudinally monitored and used to detect retinal vascular occlusive disease. Certain examples provide a retinal vascular occlusion protocol to be used with this system. In addition, certain examples provide real-time (or substantially real-time given transmission, processing, and/or storage latency) monitoring of retinal vascular occlusions with RB and OCT and OCTA. As described above, such systems and methods provide many benefits compared with problems and limitations in traditional approaches. Certain examples precisely and consistently create vascular occlusions in retina, which enables studies for diagnosis and treatment of retinal vascular occlusive disease.

Example Software and Computer Systems

In various examples, methods and systems described and disclosed herein may further include software programs on computer systems and use thereof. Accordingly, computerized control for the synchronization of system functions such as laser system operation, fluid control function, and/or data acquisition steps are within the bounds of the present disclosure. The computer systems may be programmed to control the timing and coordination of delivery of sample to a detection system, and to control mechanisms for diverting selected samples into a different flow path. In some examples of the invention, the computer may also be programmed to store the data received from a detection system and/or process the data for subsequent analysis and display.

Figure 8:
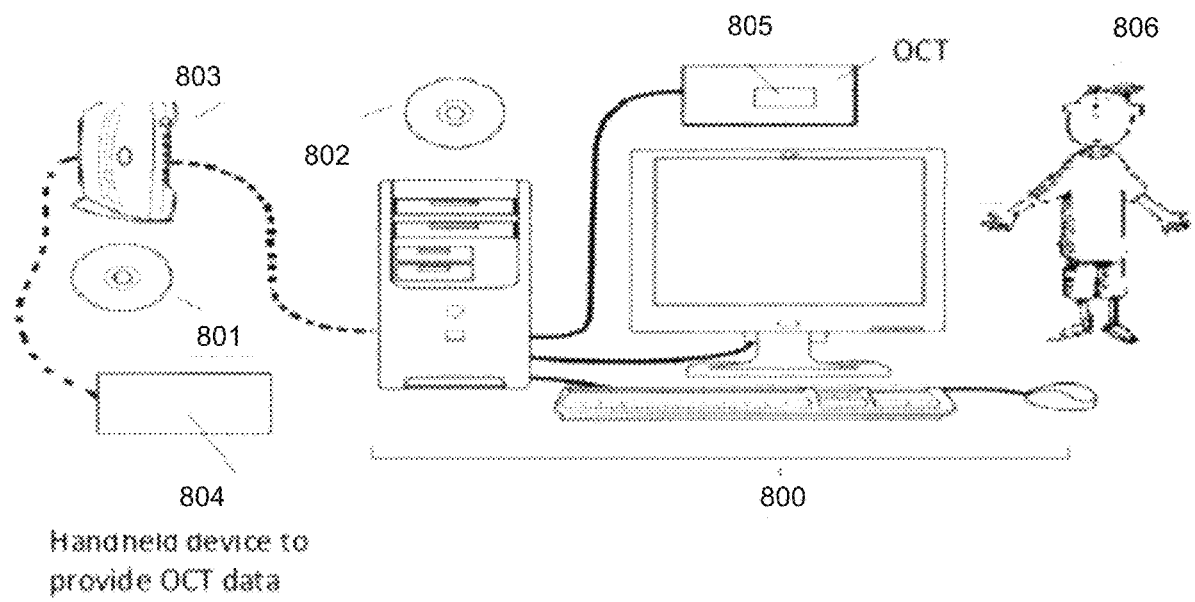

The computer system 800 illustrated in FIG. 8 may be understood as a logical apparatus that can read instructions from media 801, 802 and/or a network port, which can optionally be connected to server 803 having fixed media 801, 802. The system, such as shown in FIG. 8 can include a CPU, disk drives, optional input devices such as handheld devices for acquiring OCT objective focal length free flow measurement data 804 or other instrument types such as a laboratory or hospital-based instrument 805. Data communication can be achieved through the indicated communication medium to a server at a local or a remote location. The communication medium can include any device for transmitting and/or receiving data. For example, the communication medium can be a network connection, a wireless connection or an internet connection. Such a connection can provide for communication over the World Wide Web and/or a private network, etc. It is envisioned that data relating to the present disclosure can be transmitted over such networks or connections for reception and/or review by a party 806 as illustrated in FIG. 8.

Figure 9:
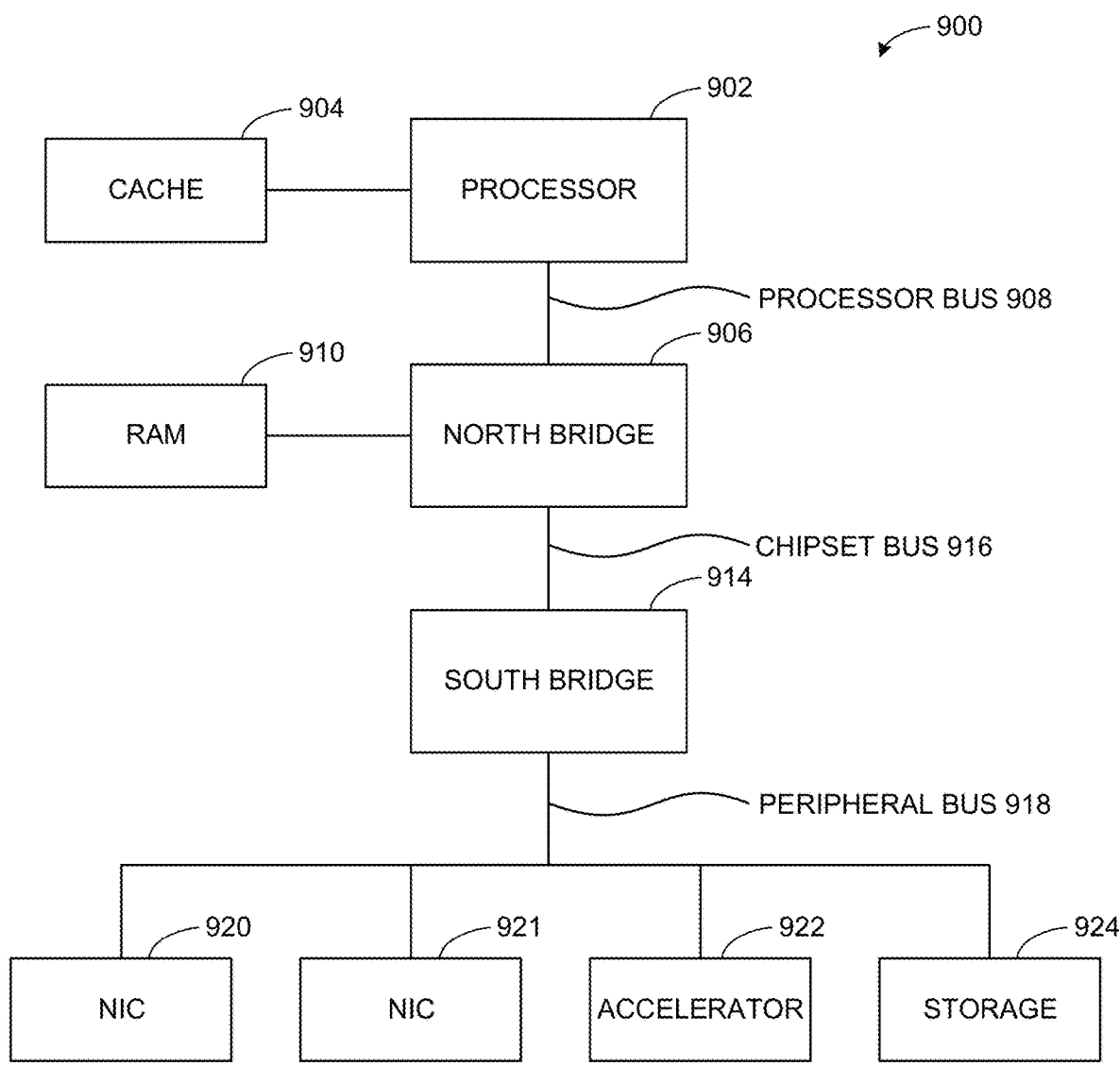

FIG. 900 is a block diagram illustrating a first example architecture of a computer system 900 that can be used in connection with examples disclosed and described herein. As depicted in FIG. 9, the example computer system can include a processor 902 for processing instructions. Non-limiting examples of processors include: Intel Xeon™ processor, AMD Opteron™ processor, Samsung 32-bit RISC ARM 1176JZ(F)-S v1 .O™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some examples, multiple processors or processors with multiple cores can also be used, whether in a single computer system, in a cluster, or distributed across systems over a network comprising a plurality of computers, cell phones, and/or personal data assistant devices.

As illustrated in FIG. 9, a high-speed cache 904 can be connected to, or incorporated in, the processor 902 to provide a high-speed memory for instructions or data that have been recently, or are frequently, used by processor 902. The processor 902 is connected to a north bridge 906 by a processor bus 908. The north bridge 906 is connected to random access memory (RAM) 910 by a memory bus 912 and manages access to the RAM 910 by the processor 902. The north bridge 906 is also connected to a south bridge 914 by a chipset bus 916. The south bridge 914 is, in turn, connected to a peripheral bus 918. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 918. In some alternative architectures, the functionality of the north bridge can be incorporated into the processor instead of using a separate north bridge chip.

In some examples, system 900 can include an accelerator card 922 attached to the peripheral bus 918. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 924 and can be loaded into RAM 910 and/or cache 904 for use by the processor. The system 900 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with certain examples.

In this example, system 900 also includes network interface cards (NICs) 920 and 921 connected to the peripheral bus for providing network interfaces to external storage, such as Network Attached Storage (NAS) and other computer systems that can be used for distributed parallel processing.

FIG. 10 is a diagram showing a network 1000 with a plurality of computer systems 1002a, and 1002b, a plurality of cell phones and personal data assistants 1002c, and Network Attached Storage (NAS) 1004a, and 1004b. In some examples, systems 1002a, 1002b, and 1002e can manage data storage and optimize data access for data stored in Network Attached Storage (NAS) 1004a and 1004b. A mathematical model can be used for the data and be evaluated using distributed parallel processing across computer systems 1002a, and 1002b, and cell phone and personal data assistant systems 1002c. Computer systems 1002a, and 1002b, and cell phone and personal data assistant systems 1002c can also provide parallel processing for adaptive data restructuring of the data stored in Network Attached Storage (NAS) 1004a and 1004b. FIG. 10 illustrates an example only, and a wide variety of other computer architectures and systems can be used in conjunction with the various examples of the present invention. For example, a blade server can be used to provide parallel processing. Processor blades can be connected through a back plane to provide parallel processing. Storage can also be connected to the back plane or as Network Attached Storage (NAS) through a separate network interface.

In some example examples, processors can maintain separate memory spaces and transmit data through network interfaces, back plane or other connectors for parallel processing by other processors. In other examples, some or all of the processors can use a shared virtual address memory space.

The above computer architectures and systems are examples only, and a wide variety of other computer, cell phone, and personal data assistant architectures and systems can be used in connection with example examples, including systems using any combination of general processors, co-processors, FPGAs and other programmable logic devices, system on chips (SOCs), application specific integrated circuits (ASICs), and other processing and logic elements. In some examples, all or part of the computer system can be implemented in software or hardware. Any variety of data storage media can be used in connection with example examples, including random access memory, hard drives, flash memory, tape drives, disk arrays, Network Attached Storage (NAS) and other local or distributed data storage devices and systems.

In some examples of present disclosure, the computer system can be implemented using software modules executing on any of the above or other computer architectures and systems. In other examples, the functions of the system can be implemented partially or completely in firmware, programmable logic devices such as field programmable gate arrays, system on chips (SOCs), application specific integrated circuits (ASICs), or other processing and logic elements.

What is claimed is:

1. An integrated optical coherence tomography (OCT) and scanning laser ophthalmoscope (SLO) apparatus, the apparatus comprising: an OCT subsystem to acquire baseline OCT and OCT angiography (OCTA) volumes of a subject without dye before occlusion and subsequent OCT and OCTA volumes of the subject with dye after occlusion; an SLO subsystem including a controller to adjust a laser; wherein the SLO subsystem is configured to provide an angiography protocol and an actinic protocol; wherein the angiography protocol of the SLO subsystem is configured to obtain fluorescence angiograms and the actinic protocol of the SLO subsystem is configured to form a vascular occlusion at a location on a target vessel of the subject; wherein a power of the laser is higher for the actinic protocol than for the angiography protocol; and a processor to process the OCT and OCTA volumes and feedback from the OCT subsystem and the SLO subsystem to determine a change in three-dimensional vasculature from before the vascular occlusion to after the vascular occlusion.

2. The apparatus of claim 1, wherein the dye includes a photosensitive Rose Bengal solution to be injected into the subject.

3. The apparatus of claim 1, wherein the SLO subsystem includes scanning mirrors to direct the laser to the location on the target vessel.

4. The apparatus of claim 1, wherein the SLO subsystem is to evaluate a first blood flow pattern before occlusion and a second blood flow pattern after occlusion to evaluate formation of the vascular occlusion.

5. The apparatus of claim 1, wherein the SLO subsystem includes a neutral density filter wheel to control a power of the laser.

6. The apparatus of claim 1, wherein the OCT subsystem is to detect backscattered photons by low-coherence interferometry to form the OCT and OCTA volumes, and wherein the SLO subsystem is to collect fluorescence in blood flow from the dye.

7. The apparatus of claim 1, wherein the SLO subsystem is to adjust a field of view to encompass a width of the target vessel before forming the vascular occlusion.

8. The apparatus of claim 1, wherein the processor is to form a model of the subject using the OCT and OCTA volumes and feedback from the OCT subsystem and the SLO subsystem.

9. The apparatus of claim 1, wherein the subject includes an eye.

10. The apparatus of claim 1, wherein at least one of the subsequent OCT and OCTA volumes is to be obtained one day after the vascular occlusion.

11. The apparatus of claim 1, wherein the power of the laser is 25-35 mW for the actinic protocol of the SLO subsystem.

12. The apparatus of claim 1, wherein the SLO subsystem is further configured to monitor the vascular occlusion after the vascular occlusion is formed.

13. A method comprising:
acquiring, using an integrated optical coherence tomography (OCT) and scanning laser ophthalmoscope (SLO) apparatus, baseline OCT and OCT angiography (OCTA) volumes of a subject;
selecting a target blood vessel using the baseline OCT and OCT angiography (OCTA) volumes of the subject;
injecting a photosensitive dye into the target blood vessel;
visualizing the photosensitive dye in the target blood vessel using fluorescence angiograms obtained via an angiography protocol of a SLO subsystem of the apparatus;
controlling, using the integrated OCT and SLO apparatus, a laser to form a vascular occlusion at a location on the target blood vessel using an actinic protocol of the SLO subsystem; wherein a power of the laser is higher for the actinic protocol than for the angiography protocol of the SLO subsystem;
acquiring, using the integrated OCT and SLO apparatus, one or more subsequent OCT and OCTA volumes of the subject after the vascular occlusion;
processing the OCT and OCTA volumes and feedback from the integrated OCT and SLO apparatus to determine a change in three-dimensional vasculature from before the vascular occlusion to after the vascular occlusion.

14. The method of claim 13, wherein the dye includes a photosensitive Rose Bengal solution to be injected into the subject.

15. The method of claim 13, further including evaluating a first blood flow pattern before occlusion and a second blood flow pattern after occlusion to evaluate formation of the vascular occlusion.

16. The method of claim 13, further including adjusting a field of view to encompass a width of the target vessel before forming the vascular occlusion.

17. The method of claim 13, further including forming a model of the subject using the OCT and OCTA volumes and feedback from the integrated OCT and SLO apparatus.

18. The method of claim 13, wherein at least one of the one or more subsequent OCT and OCTA volumes is to be obtained one day after the vascular occlusion.

19. The method of claim 13, wherein the power of the laser is 25-35 mW for the actinic protocol of the SLO subsystem.

20. The method of claim 13, further comprising monitoring the vascular occlusion using the SLO subsystem.

21. At least one computer-readable storage medium including instructions that, when executed, cause at least one processor to at least:
generate a location on a target vessel to control a laser in a scanning laser ophthalmoscope (SLO) to form a vascular occlusion at the location; wherein the vascular occlusion is formed using an actinic protocol of the SLO;
process first data acquired from optical coherence tomography (OCT) and OCT angiography (OCTA) volumes including the target vessel obtained before the vascular occlusion in contrast with second data acquired from OCT and OCTA volumes including the target vessel obtained after the vascular occlusion to determine a change in three-dimensional vasculature from before the vascular occlusion to after the vascular occlusion; wherein the subject is to be injected with a photosensitive dye before the vascular occlusion is formed; and wherein the dye is visualized using fluorescence angiograms obtained using an angiography protocol of the SLO; wherein a power of the laser is higher for the actinic protocol than for the angiography protocol; and
generate a model of a subject including the target vessel based on the first data, the second data, and the change in the three-dimensional vasculature.

22. The at least one computer-readable storage medium of claim 21, wherein the instructions, when executed, further cause the at least one processor to evaluate a first blood flow pattern before occlusion and a second blood flow pattern after occlusion to evaluate formation of the vascular occlusion.

23. The at least one computer-readable storage medium of claim 21, wherein the instructions, when executed, further cause the at least one processor to trigger an adjustment of a field of view of the laser of the SLO to encompass a width of the target vessel before forming the vascular occlusion.

* * * * *

UNITED STATES PATENT AND TRADEMARK OFFICE
CERTIFICATE OF CORRECTION

PATENT NO. : 10,750,943 B2
APPLICATION NO. : 16/005093
DATED : August 25, 2020
INVENTOR(S) : Soetikno et al.

It is certified that error appears in the above-identified patent and that said Letters Patent is hereby corrected as shown below:

In the Specification

Column 1, Line 15, Please replace the STATEMENT REGARDING FEDERALLY SPONSORED RESEARCH FOR DEVELOPMENT paragraph to read as follows:
--This invention was made with government support under grant numbers DK108248, EY026472, EY026078 and EY022883 awarded by the National Institutes of Health. The government has certain rights in the invention.--

Signed and Sealed this
First Day of November, 2022

Katherine Kelly Vidal
*Director of the United States Patent and Trademark Office*